United States Patent

Venturello et al.

[11] Patent Number: 5,117,049
[45] Date of Patent: May 26, 1992

[54] NITROGEN-CONTAINING PEROXYCARBOXYLIC MONOPERSULFATES

[75] Inventors: Carlo Venturello, Novara; Claudio Cavallotti, Milan; Fiorella Achilli, Agazzano, all of Italy

[73] Assignee: Ausimont S.r.L., Milan, Italy

[21] Appl. No.: 718,915

[22] Filed: Jun. 24, 1991

Related U.S. Application Data

[63] Continuation of Ser. No. 346,465, May 2, 1989, abandoned.

[30] Foreign Application Priority Data

May 4, 1988 [IT] Italy .................. 20455 A/88

[51] Int. Cl.⁵ ........................................... C07C 179/133
[52] U.S. Cl. .................................................. 562/2
[58] Field of Search ...................................... 562/2

[56] References Cited

U.S. PATENT DOCUMENTS 4,634,551 1/1987 Burns et al. ............................ 562/02

OTHER PUBLICATIONS

Aoyanagi et al, *Chemical Abstracts*, vol. 111, no. 176804q (1989).

Primary Examiner—Bruce Gray
Attorney, Agent, or Firm—Morgan & Finnegan

[57] ABSTRACT

Amino-derivative (poly)peroxycarboxylic acid monopersulfates having the formula:

$$HSO_5-R-\overset{R_1}{\underset{R_2}{N^+}}-(CH_2)_n-\overset{O}{\underset{}{C}}OOH \quad (I)$$

wherein the symbols have the following meanings:
R, $R_1$ and $R_2$, which may be alike or different from one another, represent hydrogen atoms, alkyl groups which may be optionally substituted with the proviso that at least one of them is a hydrogen atom;
n is an integer different from 0;
said $-(CH_2)_n-$ group may be also interrupted by $CONR_3$ groups;
and wherein $R_3$ represents a hydrogen atom or an alkyl or aryl group. A process for their preparation and their use as bleaching agents are also disclosed.

6 Claims, No Drawings

NITROGEN-CONTAINING PEROXYCARBOXYLIC MONOPERSULFATES

This is a continuation of co-pending application Ser. No. 07/346,465, filed on May 2, 1989, now abandoned.

DESCRIPTION OF THE INVENTION

The present invention relates to per se new organic (poly)peroxyacid monopersulfates, which may be referred to as (poly)peroxycarboxylic amino-derivative acid monopersulfates, and to a process for preparing same.

More particularly, the present invention relates to peroxycarboxylic amino-derivative acid monopersulfates having the formula (I):

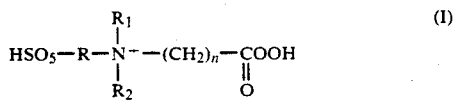

wherein the symbols have the following meanings:
R, $R_1$ and $R_2$, which may be alike or different from one another, represent hydrogen atoms, alkyl groups which may be optionally substituted, with the proviso that at least one of them is a hydrogen atom;
n is an integer different from 0,
said —$(CH_2)_n$— group may be also interrupted by CONR$_3$ groups, and wherein $R_3$ represents a hydrogen atom or an alkyl or aryl group.

The invention also relates to a process for their preparation, and to their use as bleaching agents.

The peroxycarboxylic amino-derivative compounds having the above formula (I) are per se novel, and constitute a new class of highly interesting products from an industrial viewpoint, with particular reference the high content of active oxygen per unit weight.

They, in fact, may find a general use, similarly to already known peroxyacids, in the field of plastic materials as monomer polymerization initiator agents, and, in particular, as oxidizing agents for olefin epoxidation and hydroxylation, and in many other oxidative processes in the field of fine chemistry.

In a more specific way, however, the amino-derivative (poly)peroxycarboxylic acid monopersulfates having the above formula (I) find a particularly efficacious application in the field of bleaching, in the detergent industry.

In past years, the organic peroxyacids aroused an increasing interest in the industrial field, particularly due to their excellent possibilities for use as bleaching agents in compositions for medium low temperature washing, and somewhat also due to energy-saving considerations.

Therefore there exists considerable research activity aiming to discover organic peroxyacid compounds endowed with the necessary requisites of bleaching activity, of thermal stability, and of storage stability or shelf life; these latter requisites being essential for the industrial exploitation and widespread application of such compounds.

Therefore many either mono- or di-peroxycarboxylic, straight or cyclic, organic peroxyacids are known and used, among others, in the detergent field.

Already described peroxycarboxylic acids are, e.g.: diperoxydodecanedioic acid, monoperoxyphthalic acid, diperazelaic acid, and substituted diperoxyglutaric and adipic acids, etc.

The conventional percarboxylation process contemplates the oxidation of the substrate with a solution of hydrogen peroxide in concentrated $H_2SO_4$.

The above method, when applied on substrates containing salifiable nitrogen atoms of a basic character, confers on the same substrate a high solubility in strongly acid media. This high solubility makes it impossible to apply any of the traditional processes of isolation of the peroxycarboxylic acid derivative which may be formed, such as precipitation and extraction with an organic solvent.

Surprisingly, it has been discovered in accordance with the present invention that amino-derivative (poly)peroxycarboxylic acid monopersulfates having the formula (I), salified on the nitrogen atom with the persulfuric anion, may be obtained in a stable form by means of the novel process of the present invention.

Therefore, an object of the present invention is to provide, as per se novel compounds, the amino-derivative (poly)peroxycarboxylic acid monopersulfates having the above formula (I).

Another object of the invention is to provide a simple and cheap process for the preparation of peroxycarboxylic acids having the above formula (I) in a per se stable form.

A further object of the present invention is the use of the amino-derivative peroxycarboxylic acid monopersulfates having the above formula (I) as bleaching agents in detergent formulations, in particular those destined for low-medium temperature use.

These, and still other objects which will become even clearer to those skilled in the art from the following detailed disclosure, are achieved, according to the present invention, by the amino-derivative (poly)peroxycarboxylic acid monopersulfates having the above formula (I), and by the relevant preparation process, characterized in that a substrate constituted by an amino-derivative (poly)carboxylic acid or its N-sulfate salt, corresponding to the desired peroxycarboxylic acids having carboxylic acid or its N-sulfate salt, corresponding to the desired peroxycarboxylic acids having formula (I), is reacted with $H_2O_2$ in concentrated $H_2SO_4$ and in that the peroxycarboxylic acid monopersulfate (I) is then separated from the reaction mixture by the addition of an organic solvent selected from tetrahydrofuran and ethyl acetate.

In this way peroxycarboxylic acids having the formula (I) are obtained, generally as solids, salified on their nitrogen atom with the $HSO_5$ anion, by their insolubilization in the reaction medium by the solvent.

Defined in a more explicit way, the process according to the present invention consists or consists essentially in the peroxycarboxylation reaction of the substrate consisting or consisting essentially of the (poly)acid, or its N-sulfate, corresponding to the desired acid of formula (I), in an acid medium by concentrated $H_2SO_4$, with $H_2O_2$ and in the subsequent addition, at the end of the reaction, of a suitable organic solvent, which is not miscible with the desired product by dissolving it, and which is capable, on the contrary, of completely dissolving the acid reaction medium (concentrated $H_2SO_4$), as well as the excess of $H_2O_2$ with the reaction water. This involves the consequent separation of the (poly)peroxycarboxylic acid monopersulfate product having the formula (I), in a stable solid form.

As indicated above, the substrate used as the starting material, corresponding to the (poly)peroxycarboxylic acid having the formula (I), may be constituted by an amino derivative carboxylic acid, optionally already salified as the sulfate on the nitrogen atom.

The substrates used as the starting material are per se known, and/or can be prepared according to conventional techniques.

The thus obtained product is then filtered, washed with the solvent, dried, and so forth, according to per se known techniques.

Referring to the above formula (I), R, $R_1$ and $R_2$, the same or different from one another, are constituted by hydrogen atoms or linear or branched alkyl groups preferably containing from 1 to 10 carbon atoms, which may be optionally substituted, with the proviso that at least one of them be a hydrogen atom, n is an integer different from 0, and preferably between 6 and 18.

Finally, the $—(CH_2)n—$ groups may be interrupted by at least one $—CONR_3—$ group, wherein $R_3$ represents a lower alkyl ($C_1$-$C_5$) group, an aryl group, or a hydrogen atom.

According to a preferred operating mode, the peroxycarboxylation reaction of the amino-derivative (poly)-carboxylic acids used as the starting substrates, or their N-sulphates, is carried out by gradually adding $H_2O_2$, having a concentration within the range of from approximately 70% to approximately 90% by weight, to a solution of the substrate in concentrated $H_2SO_4$ (96-98%) by maintaining the reaction temperature throughout the course of the reaction at values between approximately 0° and 20° C.

In the alternative, it has been discovered that it is possible to proceed to the previous preparation of the salified substrate as $H_2SO_4$ salt by operating, in the absence of $H_2O_2$, under the same conditions as described above, and by separating the thus-obtained salt which is then peroxidated.

The amount of $H_2SO_4$, determined at a concentration of 100%, is at least 5 moles per each mole of substrate, and is preferably between approximately 6 and 7 moles.

The hydrogen peroxide is used in an amount which is in excess with respect to the substrate, and equals at least 6 moles per each substrate mole, and preferably between 7 and 10 moles per each mole of substrate.

The reaction time depends on the nature of the substrate, on the operating temperature, and on the final total $H_2SO_4/H_2O$ molar ratio present at the end of the reaction. Said ratio is between approximately 1.2 and 1.4 by adjusting the various involved parameters.

Reaction times between approximately 30 minutes and 2 hours have been demonstrated to be operative.

The amount of tetrahydrofuran or ethyl acetate solvent used is usually not lower than 4 liters/substrate mole, such as, for example, 5 liters mole; furthermore, it is added at a temperature not higher than approximately 10° C.

The amino-derivative peroxycarboxylic acid monopersulfates having formula (I) are usually solid at room temperature. They are particularly useful in formulation of detergent compositions, e.g., granular formulations, as bleaching agents in solution over a wide temperature range.

The detergent compositions may be formulated according to the usual pertinent techniques, together with other components and/or additives, etc.

EXAMPLES

The present invention is now described in even greater detail in the following examples, which are supplied merely for illustrative purposes.

The products prepared in the examples were characterized by elemental analysis by determining their content of active oxygen (by iodometric titration), and by using Fourier Transform Infrared Spectroscopy (FT-IR).

EXAMPLE 1

4 g (0.0164 mole) of N, N-dimethylaminolauric acid were, slowly and under stirring, added to 2.5 g of sulphuric acid into a 25 ml beaker, care being taken to maintain the temperature at about 40° C. by the use of a cooling bath, and the continued at 35°-40° C., up to complete dissolution, stirring was for 1 hour.

The reaction mixture was then poured into 150 ml of ethyl acetate maintained under stirring at 10° C. The stirring was continued for 30 minutes.

The separated N, N-dimethylaminolauric acid sulfate was filtered over a porous septum, washed first with ethyl acetate (2×30ml), then with Et20 (3×30 ml), then dried under vacuum at room temperature over $CaCl_2$.

4.4 g of product were obtained, which are used for preparing the corresponding peracid monopersulfate.

3.6 g of $H_2SO_4$ at 96% (0.0352 mole) were introduced into a beaker equipped with a stirrer, a thermometer and an outer bath.

2 g of N, N-dimethylaminolauric acid sulfate (0.0059 mole) were added under stirring and at 15° C. 2.2 g of $H_2O_2$ at 85% (0.055 mole) were then added so as to not exceed +15° C.

The stirring was continued at +15° C. for 1 hour. At the end, the reaction mixture was poured into 50 ml of ethyl acetate, and maintained under stirring at $-10°$ C. After 30 minutes, the separated crystalline product was filtered over a porous septum, under vacuum, and was washed with 2×30 ml of ethyl acetate and then with 2×30 ml of ethyl ether.

Finally, the product was dried for 1 hour under vacuum at room temperature in a $CaCl_2$ drier.

1.8 g of crystalline N, N-dimethylaminoperlauric acid monopersulfate were obtained having an active oxygen content of 8.42% (98.4% of the theoretical value).

Yield: 80%

Elemental Analysis Computed for $C_{14}H_{31}NSO_8$: C, 45.02%; H, 8.36%; N, 3.75%; O (active), 8.56%; $H_2SO_5$, 30.54%.

Found: C, 45.23%; H, 8.58%; N, 3.71%; O(active), 8.42%; $H_2SO_5$, 29.9%.

Melting point: 45° C. (with decomposition).

EXAMPLE 2

2.8 g of $H_2O_2$ at 85% (0.07 mole) were added under stirring to 5.7 g of $H_2SO_4$ at 96% (0.056 mole), while maintaining the temperature below +5° C.

2 g of 12-aminolauric acid (0.0093 mole) were then added by maintaining the temperature at about +15° C. The stirring was continued at +15° C. for 1 hour. The reaction mixture was poured into 50 ml of ethyl acetate, and by then proceeding according to the procedure of Example 1.

3 g of crystalline 12-aminoperlauric acid monopersulfate were obtained having an active oxygen content of 8.95% (96.7% of the theoretical value).

Yield: 90%.

Elemental Analysis

Computed for $C_{12}H_{27}NSO_8$: C, 41.72%; H, 7.88%; N, 4.05%; O (active), 9.26%; $H_2SO_5$, 33.02%. Found: C, 41.69%; H, 7.92%; N, 4.03%; O (active), 8.95%; $H_2SO_5$, 33.01%.

Melting point: 73° C. (with decomposition).

EXAMPLE 3

6.8 g of $H_2O_2$ at 85% (0.17 mole) were added under stirring at 21.5 g of $H_2SO_4$ at 96% (0.211 mole) so as to maintain the temperature below +5° C. 2 g of B alanine (0.0224 mole) were then added by containing the exothermic reaction at about +15° C. The stirring was then continued at 15° C. for 1 hour.

The reaction mixture was then poured into 100 ml of ethyl acetate, by proceeding as described as in Example 1.

4.3 g of product were obtained having an active oxygen content of 12.5% equal to about 80% of 3-aminoperpropionic acid monopersulfate.

Elemental Analysis

Computed for $C_3H_9NSO_8$: O (active), 14.6%; $H_2SO_5$, 52.05%; Total S, 14.6%.

Found: $H_2SO_5$, 41.60%; O (active), 12.5%; Total S, 14.78%.

Melting point: 82° C. (with decomposition).

EXAMPLE 4 (Application Example)

Bleaching tests were carried out with a novel nitrogen-containing peroxyacid monopersulfate reported in Tables 1 and 2 below, at an alkaline pH (Table 1) and at acid pH (Table 2), in comparison to:

H 48 (Mg salt of monoperphthalic acid), a commercial peracid known in the detergent field, manufactured by INTEROX Chemical Ltd., London, U.K. (Tables 1 and 2).

All tests were carried out at the constant temperature of 60° C., with an initial concentration of total active oxygen in the bleaching equal for all products, and equal to 200 mg/l.

For each test, 500 ml of deionized water, contained inside a 1,000 ml flask equipped with a condenser, was heated to a temperature of 60° C. and to a pH value of 9.5 [with NaOH) (Table 1) and to a pH value of 3-4 (with a few drops of diluted $H_2SO_4$) (Table 2); then the bleaching product was additioned with stirring with the amounts reported in the following Tables, and immediately after two cotton specimens of 10 cm x 10 cm stained with standard stains of red wine at EMPA INSTITUTE of St. Gallen (Switzerland), and marked by the "EMPA 114" mark, were added.

The system was subsequently kept stirred for 60 minutes and, at the end of this time, the specimens, rinsed under running water, were dried and ironed, and were then subjected to evaluation of the bleaching effect by means of measurements of white degree by reflectometry; the results are reported in Tables 1 and 2 below, wherein the data are expressed as Bleaching %, defined as:

$$\text{Bleaching \%} = \frac{A - B}{C - B} \times 100$$

wherein:

A = degree of white (%) of the bleached specimen after the test;
B = degree of white (%) of the specimen before the test;
C = degree of white (%) of the completely bleached specimen, and wherein the degrees of white were measured by means of an Elrepho Zeiss reflectometer, assuming MgO = 100% of white as reference, and using filter N. 6 ( = 464 mm.).

The data in Table 1, tests at alkaline pH, evidence that the novel peroxy acids have a bleaching power comparable with that of H 48.

Likewise, the results, expressed as Bleaching %, reported in Table 2, show that the products have a bleaching power in an acid solution that is particularly high and indeed higher than the bleaching power of H 48.

Those results are particularly surprising considering that the peroxyacid compounds generally show a very modest bleaching activity and sometimes negligible at acid pH.

TABLE 1

| | Tests at alkaline pH (9.5) | | |
|---|---|---|---|
| COMPOUND | Amounts used in the test (grams) | Initial concentration of total active oxygen (mg/l) | Bleaching (%) |
| EXAMPLE 1 (titer = 8.42% of active oxygen) | 1.19 | 200 | 80.2 |
| H 48 (titer = 5.5% of active oxygen) | 1.86 | 200 | 81.0 |

TABLE 2

| | Tests at acid pH (3-4) | | |
|---|---|---|---|
| COMPOUND | Amounts used in the test (grams) | Initial concentration of total active oxygen (mg/l) | Bleaching (%) |
| EXAMPLE 1 (titer = 8.42% of active oxygen) | 1.19 | 200 | 78.2 |
| EXAMPLE 2 (titer = 8.95% of active oxygen) | 1.12 | 200 | 78.9 |
| H 48 (titer = 5.5% of active oxygen) | 1.86 | 200 | 60.0 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. The monopersulfate of an alkylamino-derivative of a peralkanoic acid comprising the formula (I):

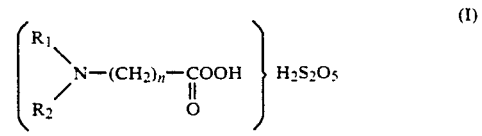

wherein the symbols have the following meanings: $R_1$ and $R_2$, which may be alike or different from each other, represent hydrogen atoms or linear or branched alkyl groups containing from 1 to 10 carbon atoms, with the promise that at least one of them is different from a hydrogen atom; n is an integer from 1 to 18.

2. The monopersulfates according to claim 1, wherein n is an integer between 6 and 18.

3. The mono-persulfate of omega-N, N-dimethyl-amino perlauric acid.

4. The monopersulfate of omegaamino-perlauric acid.

5. The monopersulfate of omegamino-perpropionic acid.

6. The monopersulfate according to claim 1, wherein the $-(CH_2)_n$-chain is interrupted by a

group, $R_3$, in its turn, being selected from H and the alkyl groups having from 1 to 5 carbon atoms.

* * * * *